US007942842B2

(12) United States Patent
Della Torre

(10) Patent No.: US 7,942,842 B2
(45) Date of Patent: May 17, 2011

(54) APPARATUS AND METHOD FOR THE TREATMENT OF BLOOD

(75) Inventor: Florenziano Della Torre, Nocera Inferiore (IT)

(73) Assignee: Freeview Ventures LLC, Houston, TX (US)

( * ) Notice: Subject to any disclaimer, the term of this patent is extended or adjusted under 35 U.S.C. 154(b) by 356 days.

(21) Appl. No.: 12/043,696

(22) Filed: Mar. 6, 2008

(65) Prior Publication Data

US 2008/0154171 A1    Jun. 26, 2008

Related U.S. Application Data

(63) Continuation of application No. 10/699,098, filed on Oct. 30, 2003, now abandoned.

(30) Foreign Application Priority Data

Oct. 31, 2002    (IT) ................ FI2002A0208

(51) Int. Cl.
*A61M 37/00*    (2006.01)
*C02F 1/44*    (2006.01)
(52) U.S. Cl. ............... 604/6.11; 604/5.01; 604/5.04; 604/6.09; 604/4.01; 604/6.13; 210/645; 210/646
(58) Field of Classification Search ........... 604/4.01, 604/5.01, 5.04, 6.09, 6.11, 7, 6.14; 210/645, 210/646, 192.2, 200, 252, 257.2, 258, 416.1, 210/321.71, 433.1, 500.21; 422/44, 45, 48
See application file for complete search history.

(56) References Cited

U.S. PATENT DOCUMENTS

| 4,666,425 A | * | 5/1987 | Fleming ............ 604/6.07 |
| 4,828,543 A | | 5/1989 | Weiss et al. |
| 5,211,849 A | | 5/1993 | Kitaevich et al. |
| 5,368,555 A | | 11/1994 | Sussman et al. |

(Continued)

FOREIGN PATENT DOCUMENTS

DE    41 13 185 C1    4/1991

(Continued)

OTHER PUBLICATIONS

Search report from European Patent Office dated Jan. 19, 2004 issued in connection with corresponding application No. EP 03025039.

(Continued)

*Primary Examiner* — Leslie R Deak
(74) *Attorney, Agent, or Firm* — Ostrolenk Faber LLP

(57) ABSTRACT

The invention relates to an apparatus and a method for the treatment of the blood in a Continuous Renal Replacement Therapy, using a machine which comprises: —connecting means from and to respective blood vessels of a patient; —blood processing means comprising a pump; —means for adding drugs or other therapeutic substances to the blood being treated; —means for feeding refill liquid into the blood; —blood filtration means, cascade-connected to one another by relative conduits, said conduits and said connecting means defining a blood path; wherein the blood to be treated passes through an oxygenating device which comprises an oxygenating membrane and is located upstream from said blood filtration means and downstream from said blood processing means, so that the blood is treated by said oxygenating membrane without the intake pressure along the portion upstream from the blood pump; and wherein the blood is pumped downstream from the connecting means to the oxygenating device at a flow rate of about 280-300 ml/min.

3 Claims, 1 Drawing Sheet

U.S. PATENT DOCUMENTS

| | | | |
|---|---|---|---|
| 5,858,238 A | 1/1999 | McRea et al. | |
| 6,561,997 B1 | 5/2003 | Weitzel et al. | |
| 6,626,857 B1 | 9/2003 | Ohta et al. | |
| 6,916,424 B2 * | 7/2005 | Collins et al. | 210/646 |
| 2002/0077581 A1 | 6/2002 | Davidner et al. | |

FOREIGN PATENT DOCUMENTS

| | | |
|---|---|---|
| EP | 0 990 444 A2 | 4/2000 |
| EP | 1 110 562 A2 | 6/2001 |

OTHER PUBLICATIONS

"Where Should the Hemofiltration Circuit Be Placed in Relation to the Extracorporeal Membrane Oxygenation Circuit?", Peter D. Yorgin, et al., *ASAIO Journal* 38 (1992) Oct./Dec., No. 4.

"Directions for New Develpments", Michael D. Klein, et al., *ASAIO Transactions,* 34 (1998) Oct./Dec., No. 4.

Abstract of German Patent No. DE 411385 dated Jul. 23, 1992.

* cited by examiner

APPARATUS AND METHOD FOR THE TREATMENT OF BLOOD

CROSS REFERENCE TO RELATED APPLICATION

This application is a continuation of U.S. application Ser. No. 10/699,098, filed Oct. 30 2003, entitled APPARATUS USABLE IN HAEMOFILTRATION TREATMENT now amended to APPARATUS AND METHOD FOR THE TREATMENT OF BLOOD, which claims priority of Italian Patent Application No. FI2002A000208, filed Oct. 31, 2002, the disclosure of which has been incorporated herein by reference.

The present invention relates to an apparatus and a method for the treatment of blood, usable, in particular, in CRRT (Continuous Renal Replacement Therapy) treatment.

BACKGROUND OF THE INVENTION

As is known, for various reasons, it may prove necessary to supplement or replace the renal function of patients to remove waste liquids and soluble substances, such as substances administered to the patient and/or waste substances contained in the blood as a result of pathology, surgery, etc.

Various procedures are employed for this purpose, including haemodialysis, haemofiltration and ultrafiltration, all of which provide for removing waste products from the patient. That is, the patient's blood is fed through filters or membranes to eliminate the waste substances in it, and is then fed back to the patient.

For patients in grave conditions, procedures include Continuous ArterioVenous Haemofiltration (CAVH), Continuous VenoVenous Haemofiltration (CVVH), or, in general, CRRT as defined above. In this type of procedure, the patient is connected permanently to the haemofiltration machine for a prolonged period of time.

Examples of known CRRT machines are described in U.S. Pat. No. 5,211,849 and U.S. Pat. No. 6,349,170. That is, a CRRT machine comprises a central unit connected at the input and output to the patient, e.g. by means of one or more catheters inserted inside corresponding blood vessels, to continuously withdraw the blood for treatment and feed back the treated blood. The central unit of a CRRT machine normally comprises a blood pump, blood heating and processing means, such as, heparin adding means, means for feeding refill liquid into the blood, and a haemofilter. The blood withdrawn continuously from the patient is thus pumped by the blood pump along the machine circuit, heparin and appropriately heated refill liquid is added, and the blood is then filtered before being fed back to the patient.

A major drawback of currently used CRRT systems is their slow speed in relation to patient requirements.

Another drawback of known CRRT systems is the compulsory use of a pump for the ultrafiltrate, which is less tolerable by chronic, haemodynamically unstable patients whose refill capacity is always unknown.

Furthermore, the known CRRT machine are relatively complex and comprising a lot of elements.

SUMMARY OF THE INVENTION

It is a main object of the present invention to eliminate the aforementioned drawbacks. According to the present invention, there is provided an apparatus and a method for the treatment of blood as claimed in the enclosed claims.

An apparatus according to the invention is for CRRT therapy of the type performable using a haemofiltration machine and which comprises: connecting means from and to respective blood vessels of a patient; blood processing means comprising a pump; means for adding drugs or other therapeutic substances to the blood being treated; means for feeding refill liquid into the blood; blood filtration means, cascade-connected to one another by relative conduits, said conduits and said connecting means defining a blood path; wherein said apparatus comprises an oxygenating device comprising an oxygenating membrane and it is located upstream from said blood filtration means and downstream from said blood processing means so that the said oxygenating membrane of the oxygenating device operates without the intake pressure along the portion upstream from the blood pump; and wherein said pump pumps the blood downstream from the connecting means to the oxygenating device at a flow rate of 280-300 ml/min.

A method according to the invention is a method for the treatment of the blood in a Continuous Renal Replacement Therapy, using a machine which comprises: connecting means from and to respective blood vessels of a patient; blood processing means comprising a pump; means for adding drugs or other therapeutic substances to the blood being treated; means for feeding refill liquid into the blood; blood filtration means, cascade-connected to one another by relative conduits, said conduits and said connecting means defining a blood path; a method wherein the blood to be treated passes through an oxygenating device which comprises an oxygenating membrane and is located upstream from said blood filtration means and downstream from said blood processing means, so that the blood is treated by said oxygenating membrane without the intake pressure along the portion upstream from the blood pump; and wherein the blood is pumped downstream from the connecting means to the oxygenating device at a flow rate of about 280-300 ml/min. The advantages of the apparatus and of the method according to the present invention substantially lie in greatly improving "decapneisation", i.e. in greatly reducing the $CO_2$ values of the blood. By way of example, reducing $FiO_2$ from 100 to 70% has been found to increase $O_2$ saturation of the patient from 92 to 100%. This is extremely important, in that the poor capacity of the lung to exchange $O_2$ constitutes a serious complication in many patients. Another advantage lies in the principle of the present invention being applicable to existing machines, which can be altered to achieve more complete, more effective performance. Moreover, the characteristics of an apparatus in accordance with the invention remain unchanged with very little maintenance.

BRIEF DESCRIPTION OF THE DRAWINGS

A non-limiting embodiment of the present invention will be described by way of example with reference to the accompanying drawing, in which.

DETAILED DESCRIPTION OF THE INVENTION

Figure 1:
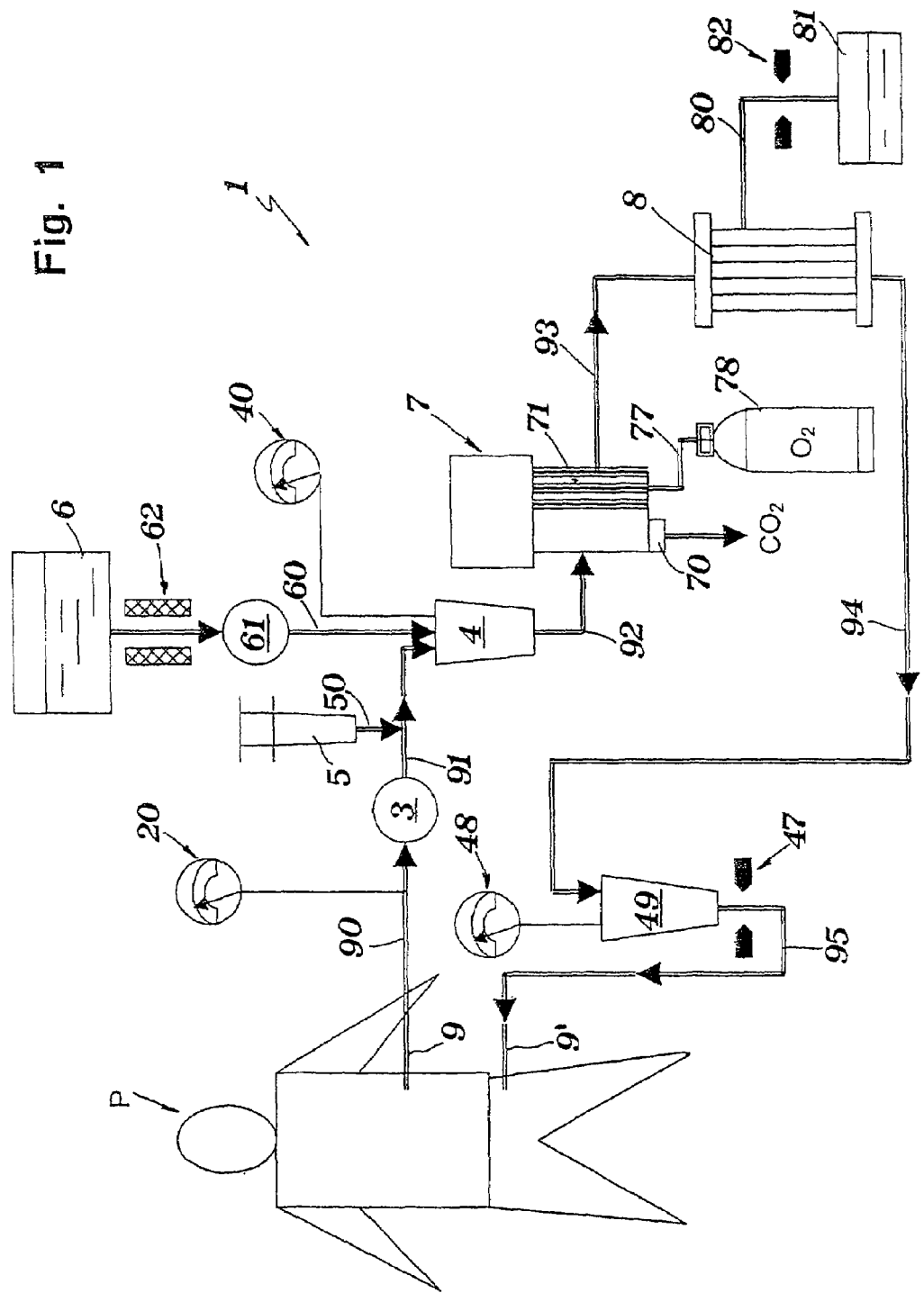
FIG. 1 shows, schematically and not to scale, one possible embodiment of a CRRT apparatus in accordance with the present invention.

Number 1 in FIG. 1 indicates as a whole a CRRT apparatus in accordance with the present invention.

Apparatus 1 is connected at the input to a patient P by a first conduit 9, which may be defined, for example, by a Horizon Medical Product DLC600 KC 11.5 Fr or DLC 800 KC femoral catheter. Other means may, of course be used to connect the apparatus to the patient, and data relative to other component parts described herein is also provided purely by way of non-limiting examples.

Catheter 9 is connected to a conduit 90, which is fitted with and acted on downstream by a blood pump 3; a gauge 20 is also provided to measure the intake arterial pressure of the patient. The successive portions of the path along which the blood flows are defined by conduit portions 91, 92, 93, 94 and 95.

Pump 3 pumps the blood downstream (in the direction shown by the arrows) to a connecting member 4, after first adding heparin by means of a conduit 50 connected to conduit 91 and to a heparin tank (syringe) 5. A conduit 60 is connected to the input of connecting member 4 to supply, by means of a pump 61, a refill liquid or infusion contained in a tank 6 and heated by heating means 62.

In is important that the apparatus has only one pump 3 because this feature allows a better treatment of the blood, with a reduced hemolysis.

A gauge 40 is provided at connecting member 4 to measure the pressure at that point along the path.

Downstream from connecting member 4, conduit portion 92 is connected to an oxygenating device 7 or "decapneisator", which may be a Jostra Polystan mycro or Jostra Safe mycro neonatal type, and which is connected by a conduit 77 to an oxygen source (i.e. a tank 78 or an oxygen supply system), and is fitted inside with an oxygenating membrane 71.

Oxygenating device 7 provides for supplying oxygen to eliminate $CO_2$ from the blood; for which purpose, $CO_2$ is eliminated through an outlet 70 of device 7 and sent to measuring means not shown.

Downstream from "decapneisator" 7, conduit portion 93 is connected to a blood filter or haemofilter 8 having an output connected to a conduit 80 for discharging ultrafiltrate into a collecting tank 81. Conduit 80 is fitted with control means 82, which may be defined, for example, by a detector for detecting blood loss in the ultrafiltrate, and which acts directly on conduit 80.

Blood filter 8 may be a currently marketed type, such as a MEDICA company MEDISULFONE D200 haemofilter.

Apparatus 1 according to the present invention advantageously does not employ an ultrafiltrate pump, in that, using oxygenating device 7, ultrafiltration takes place naturally, in a more physiologically correct manner.

Downstream from filter 8, conduit portion 94 is connected to a member 49 defined by a venous vessel and having a gauge 48 for measuring the pressure of the return blood to the patient.

Downstream from member 49, conduit portion 95—which is fitted with an air detector 47 to prevent emboli (e.g. a UABD ultrasonic air bubble detector)—is connected to a return catheter 9' for feeding the blood back to patient P.

In other words, an apparatus in accordance with the present invention comprises a CRRT machine, and an oxygenating device or "decapneisator". By way of example, the CRRT machine may be an Equasmart Medica equipped with appropriate connecting tubes, catheters, connections, etc.

Testing has revealed numerous advantages.

In particular, the apparatus is advantageous in all cases in which the oxygen concentration of the blood requires supplementing, and especially in eliminating $CO_2$ in patients in which correct substitute respiration therapy is difficult to apply.

In actual use, the apparatus is connected to the patient undergoing CVVH treatment, and a patient weight loss is set as required. For example, a total weight loss of 2400 g and an hourly loss of 100 g may be programmed. These two parameters determine a treatment time of 24 hours. Administration of an anticoagulant equal to 1.5 times the blood coagulation time may be set; in which case, a pump flow rate (QB) of 280-300 ml/min and an oxygen flow rate (QO2) of 500 ml/min will be programmed.

At therapy method level, with the present invention, the patient is connected to a CRRT machine, using an oxygenating device located and acting upstream from the blood filter and downstream from the blood pump. This location of the oxygenating device is particularly important. In fact, it means the oxygenating membranes of the oxygenating device operate without the intake (negative) pressure along the portion upstream from the blood pump, and also without the blood concentration characteristic of the venous portion, which could eventually impair their efficiency.

Again at therapy level, a weight loss (i.e. the quantity of liquid to be drained) may be set as required in each specific case, i.e. as prescribed by the physician. An anticoagulant infusion in line with standard CRRT protocols will therefore be provided, with a blood flow rate (QB) of over 300 ml/min, and an oxygen flow rate (QO2) higher than QB. It is important to continuously monitor both coagulation time, which must be kept constantly at one and a half times normal, and oxygen saturation, haematocrit, blood volume values, etc. For this purpose, a CRITE-LINE or similar apparatus may be used.

In conclusion, the present invention relates to a a procedure aimed to the continuous removal of the $CO_2$ from the blood. This procedure employs a CRRT system, and it is easily applicable in any Intensive Care Unit.

Up to day, various pathologies have been found that could benefit of the decapneization treatment; mainly in RDS (Respiratory Distress Syndrome) where it allows he forced ventilation to be kept in hyper-protective condition (where air pressure, O2 concentration and breathing frequency are within safety levels) where, besides the advantages of the reduced risk of inducted chronic distress to the patient's lungs, there is a reduced production of pro-inflammatory substances from the lungs, greatly increasing the possibility of positive evolution of the case.

Other applications are in BPCO (Chronic Bronchitis), in Post Operatoty lungs and trachea patients, for brain lesion and, in general, to avoid Pulmonary Fibrosis in all the cases of prolonged forced ventilation.

The method consists in the use of a small oxygenator (also called decapneizator) along in an extracorporeal circuit in pre-diluition with an haemo-concentrator immediately after the oxygenator itself. This allows a low blood concentration in the decapneizator thus reducing the needs for Heparin. The pressure indiced by the flow resistance of the haemo-concentrator prevents any air passage in the blood flow, furthermore the ultra filtrated fluid from the haemo-concentrator contains $CO_2$ that is easily removed by the passage in the decapneizator device.

Clearly, changes may be made to the form, dimensions, component part locations, and type of materials employed in the embodiment described and illustrated herein without, however departing from the scope of the present invention.

What is claimed is:

1. A method for the treatment of blood in a Continuous Renal Replacement Therapy comprising the step of filtering the blood of a patient with a haemofilter disposed on a blood path formed by conduits through which the blood of the patient passes, wherein:

the patient is connected to the haemofilter with a femoral catheter, which is connected to a pump, disposed upstream with respect of the haemofilter and which pumps downstream at a flow rate of about 280-300 ml/min;

said haemofilter having one output connected to a conduit configured for discharging ultrafiltrate into a collecting tank and a second output connected to the patient;

wherein the blood pumped by said pump passes through an oxygenating device comprising an oxygenating membrane located upstream from said haemofilter and downstream from said pump, so that the pumped blood is treated by said oxygenating membrane without intake pressure along the blood path upstream from the blood pump; and wherein the blood treated by the haemofilter returns to the patient without the ultrafiltrate.

2. The method of claim 1, wherein the blood and ultrafiltrate are pumped only by one pump, disposed upstream from said oxygenating device.

3. The method of claim 1, wherein the blood, downstream of said pump and upstream from said oxygenating device is returned with a refill liquid having been infusion heated by heating means.

* * * * *